United States Patent
Talkachova et al.

(10) Patent No.: US 10,258,249 B2
(45) Date of Patent: Apr. 16, 2019

(54) GRAPHICALLY MAPPING ROTORS IN A HEART USING SHANNON ENTROPY

(71) Applicants: Regents of the University of Minnesota, Minneapolis, MN (US); Mayo Foundation for Medical Education and Research, Rochester, MN (US)

(72) Inventors: Alena Talkachova, Shoreview, MN (US); Shivaram Poigai Arunachalam, Minneapolis, MN (US); Siva K. Mulpuru, Rochester, MN (US); Paul A. Friedman, Rochester, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 74 days.

(21) Appl. No.: 15/373,193

(22) Filed: Dec. 8, 2016

(65) Prior Publication Data
US 2017/0156616 A1  Jun. 8, 2017

Related U.S. Application Data

(60) Provisional application No. 62/264,650, filed on Dec. 8, 2015.

(51) Int. Cl.
*A61B 5/04* (2006.01)
*A61B 5/046* (2006.01)
(Continued)

(52) U.S. Cl.
CPC .......... *A61B 5/04012* (2013.01); *A61B 5/044* (2013.01); *A61B 5/046* (2013.01); *A61B 5/4836* (2013.01)

(58) Field of Classification Search
None
See application file for complete search history.

(56) References Cited

U.S. PATENT DOCUMENTS

| 8,825,146 B2 | 9/2014 | Li |
| 2014/0180051 A1 | 6/2014 | Thakur et al. |

(Continued)

FOREIGN PATENT DOCUMENTS

WO  2013123549 A1  8/2013

OTHER PUBLICATIONS

Masè M, Faes L, Antolini R, Scaglione M, Ravelli F. Quantification of synchronization during atrial fibrillation by Shannon entropy: validation in patients and computer model of atrial arrhythmias. Physiol Meas. Dec. 2005;26(6):911-23.*

(Continued)

*Primary Examiner* — Ankit D Tejani
(74) *Attorney, Agent, or Firm* — Brian D. Kaul; Westman, Champlin & Koehler, P.A.

(57) ABSTRACT

Disclosed herein are techniques for graphically indicating aspects of rotors (such as pivot points of rotors) associated with atrial or ventricular fibrillation. Embodiments can include receiving, using a processor, an electrogram for each of a plurality of spatial locations in a heart, each electrogram comprising time series data including a plurality of electrical potential readings over time. Embodiments can also include generating, from the time series data, an entropy dataset including a plurality of Shannon entropy values corresponding to the plurality of spatial locations in the heart. Also, examples can include generating, from the entropy dataset, an entropy map including a plurality of graphical indications of the Shannon entropy values at the plurality of spatial locations in the heart, wherein the entropy map can include an image of the heart and graphical indications of locations of aspects of rotors in the heart (such as pivot point of rotors).

17 Claims, 5 Drawing Sheets

(51) Int. Cl.
  A61B 5/044  (2006.01)
  A61B 5/00   (2006.01)

(56) References Cited

U.S. PATENT DOCUMENTS

2014/0371609 A1* 12/2014 Narayan ............... A61B 5/0006
                                                          600/508
2015/0150643 A1    6/2015 Trayanova et al.

OTHER PUBLICATIONS

Calkins et al., 2012 HRS/EHRA/ECAS Expert Consensus Statement on Catheter and Surgical Ablation of Atrial Fibrillation, Heart Rhytme 9, pp. 632-696.e21, 2012.
Chen et al., Epidemiology of atrial fibrillation: a current perspective, Heart Rhythm, vol. 4, No. 3, S1-56, 2007.
Chou et al., Epicardial ablation of rotors supresses inducibility of acetylcholine-induced atrial fibrillation in left pulmonary vein-left atrium preparations in a beagle heart failure model, Journal of the American College of Cardiology, Heart Rhythm Disorders, Vo. 58, No. 2, pp. 158-166, 2011.
Davidenko et al., Stationary and drifting spiral waves of excitation in isolated cardiac musle, Nature Voll. 355, pp. 349-351, 1992.
Earley et al., Validation of the noncontact mapping system in the left atrium during permanent atrial fibrillation and sinus rhythm, Journal of American College of Cardiology, Vo. 48, No. 3, pp. 485-491, 2006.
Elayi et al., Atrial fibrillation termination as a procedural endpoint during ablation in long-standing persistent atrial fibrillation, Hear Rhythm Society, pp. 1216-1223, 2010.
Haissaguerre et al., Spontaneous initiation of atrial fibrillation by ectopic beats originating in the pulmonary veins, The New England Journal of Medicine, vol. 339, No. 10, pp. 659-666, 1998.
Haissaguerre et al., Mapping-guided ablation of pulmonary veins to cure atrial fibrillation, The American Journal of Cardiology, vol. 86 (9A), pp. 9K-19K, 2000.
Haissaguerre et al., Catheter Ablation of Long-Lasting Persistent Atrial Fibrillation: Critical Structures for Termination, Journal of Cardiovascular Electrophysiology, vol. 16, No. 11, pp. 1125-1137, 2005.
Herweg et al., Termination of Persistent Atrial Fibrillation Resistant to Cardioversion by a Single Radiofrequency Application, PACE, vol. 26, pp. 1420-1423, 2003.
Matiukas et al., Optical Mapping of Electrical Heterogeneities in the Heart During Global Ischemia, 31st Annual International Conference of the IEEE EMBS, pp. 6321-6324, 2009.
Mironov et al., Role of Conduction Velocity Restitution and Short-Term Memory in the Development of Action Potential Duration Alternans in Isolated Rabbit Hears, Circulation 118, pp. 17-25, 2008.
Moe et al., A computer model of atrial fibrillation, American Heart Journal, vol. 67, pp. 200-220, 1964.
Narayan et al., Classifying fractionated electrograms in human atrial fibrillation using monophasic action potentials and activation mapping: evidence for localized drivers, rate acceleration, and nonlocal signal etiologies, Heart Rhytm, vol. 8, No. 2, pp. 244-253, 2011.
Narayan, et al., Treatment of Atrial Fibrillation by the Ablation of Localized Sources, Journal of the American College of Cardiology, vol. 60, No. 7, pp. 628-636, 2012.
Nattel, New ideas about atrial fibrillation 50 years on, Nature, vol. 415, pp. 219-226, 2002.
Oral et al., Circumferential pulmonary-vein ablation for chronic atrial fibrillation, The New England Journal of Medicine, vol. 354, No. 9, pp. 934-941, 2006.
Pandit et al., Rotors and the dynamics of cardiac fibrillation, Circulation Research, pp. 849-862, 2013.
Schmitt et al., Biatrial multisite mapping of atrial premature complexes triggering onset of atrial fibrillation, The American Journal of Cardiology, vol. 89, pp. 1381-1387, 2002.
Tzou et al., Termination of persistent atrial fibrillation during left atrial mapping, Journal of Cardiovascular Electrophysiology, vol. 22, No. 10, pp. 1171-1173, 2011.

\* cited by examiner

GRAPHICALLY MAPPING ROTORS IN A HEART USING SHANNON ENTROPY

CROSS-REFERENCE TO RELATED APPLICATION

The present application is based on and claims the benefit of U.S. provisional patent application Ser. No. 62/264,650, filed Dec. 8, 2015, the content of which is hereby incorporated by reference in its entirety.

FIELD

Embodiments of the present disclosure are directed to graphically indicating at least one location of a rotor or a specific type of aspect of a rotor in a heart using Shannon entropy calculations. For instance, some exemplary embodiments are directed to graphically indicating respective pivot points of rotors in a heart using Shannon entropy calculations.

BACKGROUND

Disclosed herein are techniques for rotor identification associated with atrial fibrillation (AF) or ventricular fibrillation (VF), such as to, for example, improve catheter ablation or pacing procedures in cardiac pacemakers.

Over two million people in the United States are currently afflicted with AF, which may be the most common sustained cardiac arrhythmia in humans, and many more cases are predicted in the near future. AF is also considered to be a cause of stroke.

Antiarrhythmic drugs are only partially effective and can cause serious side effects, including life-threatening arrhythmias. Despite great strides in understanding of AF, therapy using pharmacological, percutaneous and surgical interventional approaches remains suboptimal.

A limitation of therapy is the lack of mechanistic understanding for AF. However, it has recently been demonstrated that paroxysmal AF in patients is initiated by focal triggers localized usually to one of the pulmonary veins (PV) and can be remedied by a catheter-based ablation procedure. However, in persistent AF, the location of triggers is unclear; and therefore, therapy can be challenging. While advances have been made in ablating PV AF triggers in persistent and permanent forms of the arrhythmia, triggers may arise outside of PV, and extra-PV substrate plays an important role in arrhythmogenesis and maintenance of AF.

Catheter ablation is associated with limited success rates in patients with persistent AF. This may be the case because persistent AF is known to be at least partially caused by rotors, such as rotors located outside of the PV, and known mapping systems can predict locations of rotors outside of the PV in patients with persistent AF to some extent.

Known processing methods that are used to identify AF vulnerable regions of the heart include analysis of the dominant frequency (DF), complex fractionated electrograms (CFAE), phase analysis and local activation time (LAT) maps. These techniques can be based on temporal analysis of electrograms from different spatial locations of atria. However, the high frequency of recurrence of arrhythmias in patients with persistent AF after PV isolation and ablation shows that the current processing methods for AF analysis may not be adequate to predict critical areas of AF maintenance, such as locations of rotors. Also, known electro-anatomic mapping systems (such as ENSITE, NAVX, and CARTO) that employ known signal processing techniques (DF, CFAE, and LAT) may not be able to adequately predict a rotor's location outside of PV in patients with persistent AF. For example, the aforementioned mapping techniques may fail since clinical signals may not represent local activation. Also, virtual electrograms from non-contact methods may distort information in AF.

Data supports localized sources by reentrant mechanisms for AF showing that AF may be sustained by stable drivers such as electrical rotors. The pivot points of such rotor waves are believed to be good ablation targets to terminate AF in patients. About 77.8% success rate has been demonstrated by ablation of such sites in paroxysmal, persistent, and long-standing AF patients.

However, known mapping methods used for guiding catheter ablation, such as LAT maps and CFAE—mean index maps, have numerous limitations in their ability to accurately identify rotor pivot zones. This can be due to noise and misleading phase and activation times that distort these maps.

Thus, there are problems to be solved. For instance, there is room for improvement with spatiotemporal mapping technology that can identify the rotor pivot points in a patient-specific manner.

SUMMARY

Embodiments of the present disclosure include methods for graphically indicating aspects of rotors (such as pivot points of rotors) associated with atrial or ventricular fibrillation. In some exemplary embodiments, the methods include receiving, using a processor, an electrogram for each of a plurality of spatial locations in a heart. Each of the electrograms can include time series data including a plurality of electrical potential readings over time.

The methods can also include generating, from the time series data, an entropy dataset. The methods can also include generating an entropy map from the entropy dataset. The dataset can include a plurality of Shannon entropy values corresponding to the plurality of spatial locations in the heart. The map can include a plurality of graphical indications of Shannon entropy values at the spatial locations in the heart. The entropy map can also include an image of the heart and graphical indications of locations of aspects of rotors in the heart. For instance, the map can include an image of the heart and graphical indications of locations of pivot points of rotors in the heart associated with atrial or ventricular fibrillation.

In some exemplary embodiments, the plurality of electrograms or the plurality of electrical potential readings over time can be derived from an optical mapping of electrical potentials on the heart over time.

In some exemplary embodiments, the time series data of the plurality of electrograms or the plurality of electrical potential readings can be obtained from any optical mapping experiments feasible on human or animal hearts, including any in vivo or in vitro experiment.

For example, an optical mapping experiment can include a heart put through an in vitro experiment such as a Langendorff heart assay or an in vivo assay similar to the Langendorff heart assay that does not remove the heart from the organism. In one example, a certain amount of voltage-sensitive dye, such as di-4-ANEPPS (5 µg/mL), can be added to the perfusate. After staining with the dye, a laser, such as a 532 nm green laser, can be used to illuminate a part of the heart including the perfusate, such as an epicardial surface of the heart. From the illumination, visible or invisible radiation illuminated from the heart can captured with one or more sensors or cameras. An atrial or ventricular tachycardia can be induced on the heart (such as via burst pacing), and recordings of images, such as phase movies, can be obtained at parts of the heart having or expected to have rotors. The recording of images can be processed as described herein, such as by using at least Equation (1) (which is shown below), to generate an SE dataset or map.

Also, for example, an electrophysiological study can be done in vivo, such as with a patient in a postabsorptive state under general anesthesia. A part of the heart, such as the left atrium, can be accessed, such as accessed transseptally. Electro-anatomic mapping, such as fluoroscopy, can be performed. For instance, a CARTO mapping system can be used. Also, a catheter combined with a fluoroscopy sensor, such as the CARTO mapping system, can sense the 2D or 3D geometry of the part of the heart, such as a chamber of the left atrium. Reconstruction of the part of the heart virtually can be done in real time. Also, a recording system, used in the mapping, can, at different spatial locations of the heart, record the plurality of electrograms or the plurality of electrical potential readings such as from one of the sensors mentioned herein.

In some exemplary embodiments, the generating of the entropy dataset and/or map can include binning the plurality of electrograms according to amplitude, which results in a plurality of bins per binned electrogram. A bin of the plurality of bins can represent an amplitude or amplitude range and can include a frequency of occurrences of the amplitude or amplitude range. Also, in such embodiments, the generating of the entropy dataset and/or map can include determining a probability density of each bin of the plurality of bins, per binned electrogram, and determining a Shannon entropy value according to the determined probability densities, per binned electrogram.

For instance, exemplary methods can include: receiving, using a processor, an electrogram for each of a plurality of spatial locations in a heart, each electrogram including time series data including a plurality of electrical potential readings over time; binning the plurality of electrograms according to amplitude, which results in a plurality of bins per binned electrogram, wherein a bin of the plurality of bins represents an amplitude or amplitude range and includes a frequency of occurrences of the amplitude or amplitude range; determining a probability density of each bin of the plurality of bins, per binned electrogram; determining a Shannon entropy value according to the determined probability densities, per binned electrogram; and generating an entropy dataset including the entropy values. Then from the dataset a map can be derived including a plurality of graphical indications of the Shannon entropy values at spatial locations in the heart corresponding to the binned electrograms. In such examples, the entropy map can include an image of the heart and graphical indications of locations of aspects of rotors in the heart. In such embodiments, the determining of a Shannon entropy value can include using the following Equation (1):

$$SE = -\sum_{i=0}^{N-1} p_i \log_2 p_i, \quad \text{Equation (1)}$$

wherein N is a number of bins in the plurality of bins per binned electrogram, and $p_i$ is a probability of a sample reading falling within a particular bin of the plurality of bins.

The methods can also include physically changing the heart at one or more of the plurality of spatial locations in the heart according to the entropy dataset and/or map. In such an embodiment, the changing of the heart includes catheter ablations at such locations in the heart.

The methods can also include performing the plurality of electrograms at the plurality of spatial locations in the heart to obtain the time series data. The method can also include communicating the entropy dataset and/or map to a display device communicatively coupled to the processor and graphically displaying the entropy dataset and/or map by the display device. In such an embodiment, the entropy map can include a two-dimensional or a three-dimensional image of the heart, and a color, shade, symbol, or index value of a range of such elements can correspond to an amount of Shannon entropy such that the entropy map, through use of such elements, shows Shannon entropy levels at different locations in the heart. For instance, the methods can further include displaying graphical indicators of the plurality of Shannon entropy values corresponding to the plurality of spatial locations in the heart using the display device. The graphical indicators of the plurality of Shannon entropy values can include a range of different colors, a range of shades of a gray or another color, a range of different symbols, or a range of indexed values, wherein each aspect of the range can correspond to a Shannon entropy value such that the displaying of the graphical indicators of the plurality of Shannon entropy values shows Shannon entropy levels at different locations in the heart.

Also, in some exemplary embodiments, at least some of the operations of the methods can be implemented by computer executable instructions stored on a non-transitory computer readable medium.

DETAILED DESCRIPTION OF ILLUSTRATIVE EMBODIMENTS

Figure 1:
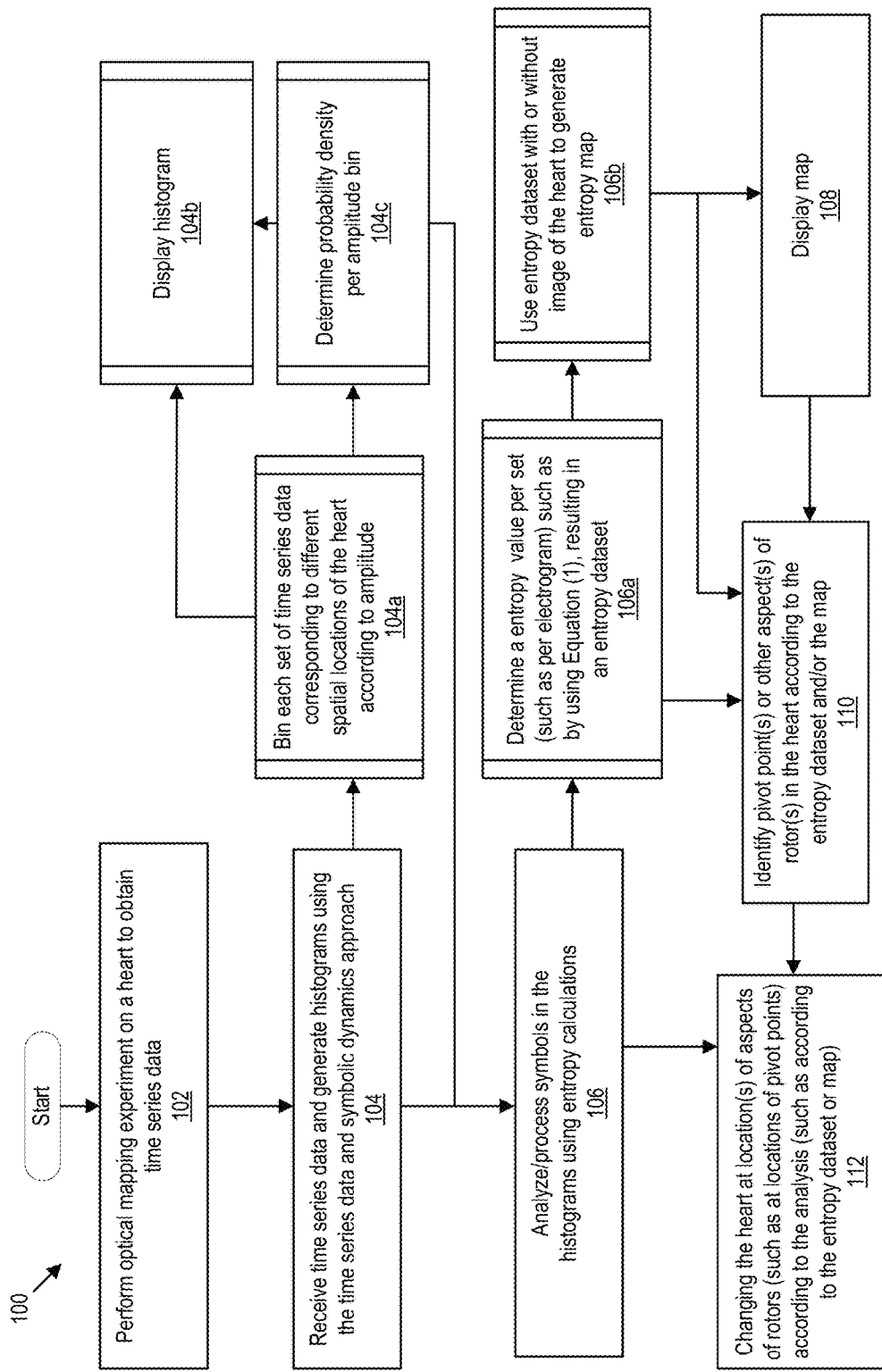
FIG. 1 illustrates example operations performed by a system that can implement rotor identification in a fibrillation, such as an atrial fibrillation.

Embodiments of the present disclosure are described more fully hereinafter with reference to the accompanying drawings. Elements that are identified using the same or similar reference characters refer to the same or similar elements. The various embodiments of the present disclosure may, however, be embodied in many different forms and the invention should not be construed as limited to only the embodiments set forth herein.

Specific details are given in the following description to provide a thorough understanding of the embodiments.

However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present disclosure.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Overview

Disclosed herein are embodiments of an entropy-based approach for identifying regions of rotors associated with AF or VF. Such techniques can produce patient-specific dynamic spatiotemporal maps of active substrates during AF or VF (such as during persistent AF). These maps can provide information during an electrophysiology study to provide guidance for patient tailored ablation therapy. Also, these techniques can overcome limitations with known mapping systems.

In an example, Shannon entropy (SE) based mapping based on a symbolic dynamics approach may be used to overcome limitations in known mapping techniques, such as one or more of those described herein. For example, SE values can be used to identify rotor cores and to produce patient-specific dynamic spatiotemporal maps of AF active substrates for patient-tailored ablation therapy.

The techniques disclosed herein, which use calculated SE values, can be used individually or in combination. Also, they can be used for identification of self-sustaining regions of chaotic rhythms in AF or VF.

The term entropy herein is the amount of disorder of a system or a part of a system. In mathematics, a more abstract definition is used, such as Shannon entropy (SE). The SE (or H(X)) of a variable X is defined as:

$$H(X) \equiv -\sum_s P(x)\log_2[P(x)]$$

where P(x) is the probability that X is in the state x, and P $\log_2$P is defined as 0 if P=0.

In one example, entropy includes the measure of information based on symbolic dynamics, which can reflect different intrinsic dynamics of different time series. This is different from the time domain and frequency domain analysis of DF, CFAE, or LAT, for example, where such dynamics are not used. Also, due to meandering of a rotor in time and space, frequency distribution of a part of the rotor, such as at a pivot point of the rotor, can be complex, and not easily to be captured by DF.

The symbolic dynamics approach can include binning electrograms or electrical potential readings over time according to amplitude, which can result in a plurality of bins per electrogram. Each bin of the plurality of bins can represent an amplitude or amplitude range of the electrical potential readings and include a frequency of occurrences of the amplitude or amplitude range of the electrical potential readings. Then, the bins may be displayed as a histogram. A probability density of each bin of the plurality of bins can be determined per electrogram. This data (including symbols of the histogram for example) can then be analyzed and/or processed using entropy calculations, such as SE calculations. A SE entropy value can be calculated based on the determined probability densities, per electrogram.

FIG. 1 illustrates example operations 100 performed by a system that can implement rotor identification in a fibrillation, such as atrial or ventricular fibrillation, and treat the fibrillation accordingly. Operations 100 form a method for identifying and treating a pivot point or some other aspect of a rotor in a fibrillation (such as an atrial or ventricular fibrillation). The operations 100 include performing an optical mapping experiment feasible on human or animal hearts, including any in vivo or in vitro experiment to obtain time series data, at 102. The time series data may be of a plurality of electrograms or a plurality of electrical potential readings captured in the experiment.

As mentioned herein, the electrograms or electrical potential readings at different locations of the heart over time may be obtained through an optical mapping of the heart. In some embodiments, the optical mapping of the heart involves mapping through optics experiments. The time series data of the plurality of electrograms or the plurality of electrical potential readings can be obtained from any optical mapping experiments feasible on human or animal hearts, including any in vivo or in vitro experiment.

For example, an optical mapping experiment can include a heart put through an in vitro experiment such as a Langendorff heart assay or an in vivo assay similar to the Langendorff heart assay that does not remove the heart from the organism. In one example, a certain amount of voltage-sensitive dye, such as di-4-ANEPPS (5 μg/mL), can be added to the perfusate. After staining with the dye, a laser, such as a 532 nm green laser, can be used to illuminate a part of the heart including the perfusate, such as an epicardial surface of the heart. From the illumination, visible or invisible radiation illuminated from the heart can captured with one or more sensors or cameras. For instance, fluorescence intensity can be captured with two 12-bit CCD cameras, which run at 1000 frames per second with 64×64 pixel resolution. An atrial or ventricular tachycardia can be induced on the heart (such as via burst pacing), and recordings of images, such as phase movies, can be obtained at parts of the heart having or expected to have rotors. The recording of images can be processed as described herein, such as by using at least Equation (1) (which is shown below), to generate an SE dataset or map.

Figure 2B:
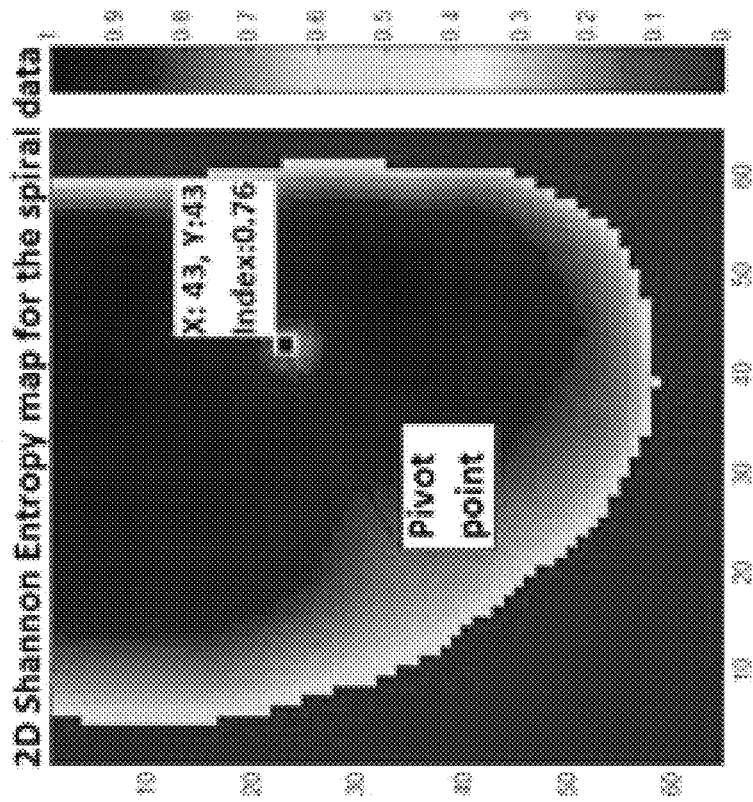
FIG. 2B shows a distribution of SE values for the rotor shown in FIG. 2A.
Figure 2A:
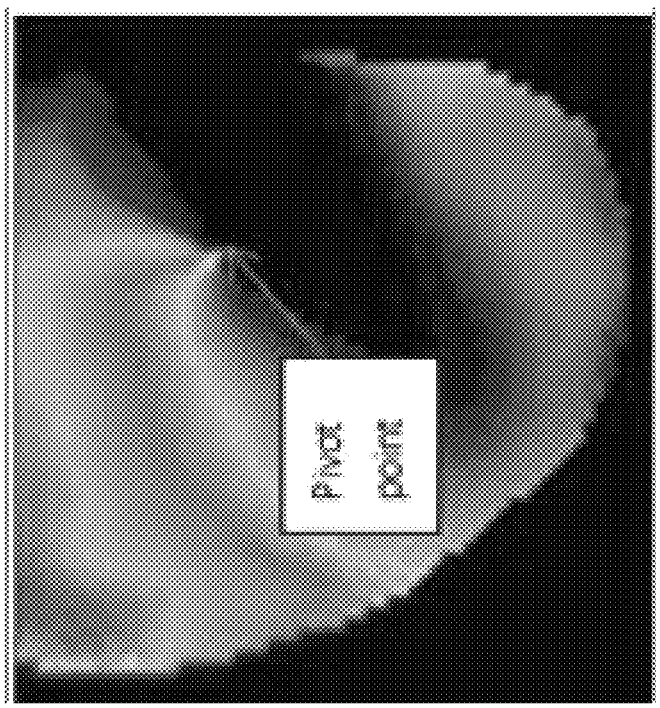
FIG. 2A illustrates example graphics identifying a rotor using a phase movie from an optical mapping animal experiment.

FIG. 2A illustrates an example of a single rotor in an isolated rabbit heart from optical mapping experiments. In FIG. 2A, the pivot point of the rotor is indicated by an arrow. FIG. 2A is an example snapshot of a phase movie, where different colors represent different phases of action potential. The convergence of different phases may correspond to a singularity point, e.g., the pivotal point or core of the rotor, which can be identified by the arrow.

Also, for example, an electrophysiological study can be done in vivo, such as with a patient in a postabsorptive state under general anesthesia. A part of the heart, such as the left atrium, can be accessed, such as accessed transseptally. In such experiments, a blood clotting treatment, such as a single bolus of 100 IU/kg heparin, can be administered and repeated to maintain activated clotting, such as for time above 190 seconds. Electro-anatomic mapping, such as fluoroscopy, can be performed. For instance, a CARTO mapping system (such as a Biosense-Webster mapping system) can be used. In such examples, the CARTO mapping system can have a sensor position accuracy of 0.8 mm and 5°. Also, a catheter combined with a fluoroscopy sensor, such as the CARTO mapping system, can sense the 2D or 3D geometry of the part of the heart, such as a chamber of the left atrium. Reconstruction of the part of the heart virtually can be done in real time. Also, a recording system, used in the mapping, can, at different spatial locations of the heart, record the plurality of electrograms or the plurality of electrical potential readings such as from one of the sensors mentioned herein. For instance, at each point of recording, a system, such as the CARTO mapping system, can record electrograms, such as 12-lead ECG and unipolar and bipolar intracardiac electrograms sampled at 977 Hz, thus allowing the electrophysiological information to be encoded, such as color coded, and superimposed on the anatomic map. Also, evenly distributed points can be recorded such as by using a fill threshold of 20 mm throughout the right atrium, left atrium, and any other pertinent part of the heart. At each point, electrograms, such as 5-15 second electrograms, together with the surface ECG, can be acquired. Endocardial contact during point acquisition can be facilitated by fluoroscopic visualization of catheter motion, the distance to geometry signaled by the catheter icon on the CARTO system, and/or in a subset with intracardiac echocardiography. A high-resolution sensing catheter, such as a high resolution PENTARAY NAV catheter, can be used in a sequential scanning approach to fully map the relevant parts of the heart, such as both atrial chambers. The raw electrograms can be filtered, such as by a bandpass filter at 30-500 Hz. They can also be exported for offline processing. The raw electrograms can exported offline and processed using software or firmware, such as custom written MATLAB software, to obtain SE. Finally, any of the electrograms or SE datasets described herein can be superimposed on the anatomic map to obtain a 2D or 3D SE map.

In some exemplary embodiments, time series data can be obtained from pre-filtered intra-atrial electrograms such as obtained from a Prucka system. These intra-atrial electrograms can be free from high frequency noise. A notch filter, such as a 60 Hz notch filter, can be used to remove noise such as line noise contamination. The electrograms can be visually inspected for ventricular far field (VFF) noise and can be verified to have minimal or no VFF contamination. Instructions, such as software or firmware based instructions like a custom MATLAB program, can be used to do the data processing described herein. Also, such electrograms can be used to compute the SE as described in Equation (1).

Referring back to FIG. 1, the operations 100 include receiving, by a processor (such as CPU 502 illustrated in FIG. 5), at 104, the time series data obtained from a plurality of electrograms or electrical potential readings of a heart. As mentioned herein, the electrograms can be derived from electrical potential readings, such as those described herein. In instances using electrograms, each electrogram of the plurality of electrograms corresponds to a different spatial location (such as a different unique spatial location) in the heart and each electrogram of the plurality of electrograms includes a plurality of electrical potential readings over a time series. These readings may be voltage readings (such as shown by chart 302a of FIG. 3). Also, different locations in the heart are represented by respective sets of data.

Additionally, at 104, the processor may generate histograms using the sets of data and the symbolic dynamics approach disclosed herein. The symbolic dynamics approach may include binning each electrogram of the plurality of electrograms (such as binning each set of electrical potentials) according to amplitude at 104a, which results in a plurality of bins per electrogram. Each bin of the plurality of bins represents an amplitude or amplitude range of the electrical potentials and includes a frequency of occurrences of the amplitude or amplitude range. At 104b, the bins may be displayed as a histogram, such as shown by histogram 302b of FIG. 3. The operation at 104 may also include determining a probability density of each bin of the plurality of bins, per electrogram, at 104c. The histogram may also be displayed after the determination of the probability densities.

At 106, the processor may analyze and/or process symbols in the histogram using entropy calculations, such as SE calculations. Operation 106 may include determining an entropy value according to the determined probability densities, per electrogram at 106a. For instance, a SE value can be calculated, such as according to the following Equation (1).

$$SE = -\sum_{i=0}^{N-1} p_i \log_2 p_i, \quad (1)$$

where N is the number of amplitude bins, and $p_i$ is the probability of any sample falling within a particular amplitude bin.

Figure 4:
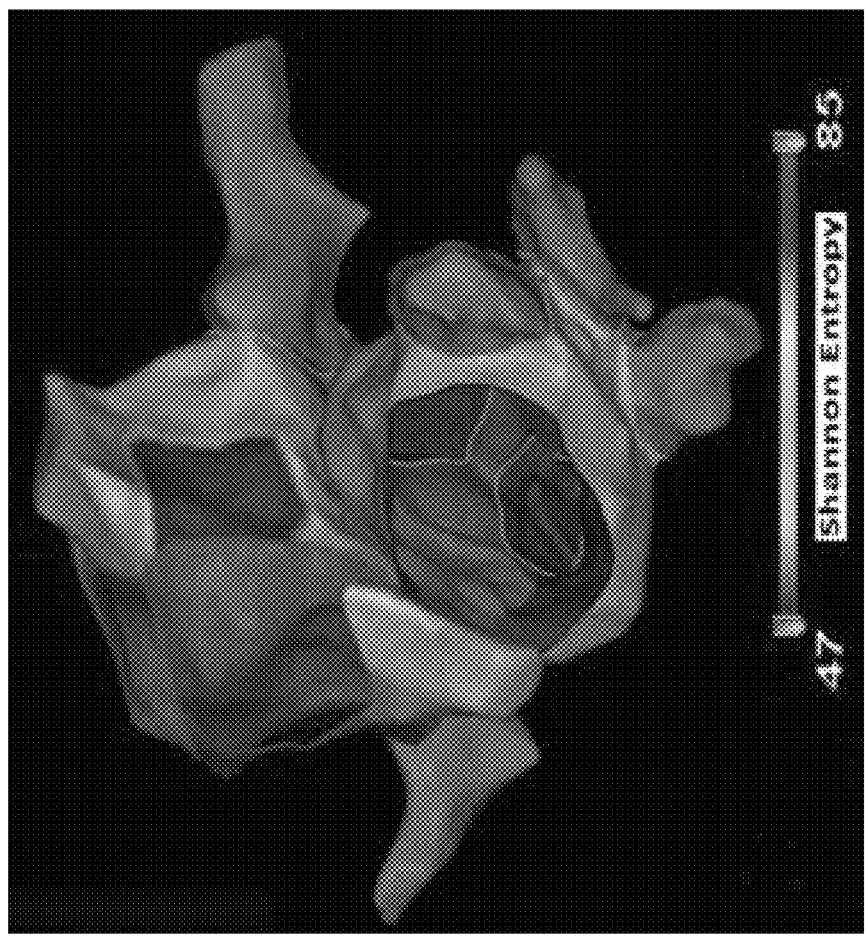
FIG. 4 illustrates an example of 3D distribution of SE values in a heart having persistent AF. Higher values of SE might show the region of a rotor.

Operation 106 may also include generating an entropy dataset at from the determination of the entropy values 106a, and/or generating an entropy map by mapping the entropy values and/or dataset to their corresponding spatial locations in the heart at 106b. Such mapping can occur over a 2D or 3D image of the heart, for example. Also, the amount of entropy per location can correspond to a color of a range colors, shades, symbols, or values such that the entropy map, through the use of such elements, shows entropy levels at different locations in the heart (such as shown by FIGS. 2B and 4).

Alternatively, or in addition to generating a map, the system can display graphical indicators of the plurality of Shannon entropy values corresponding to the plurality of spatial locations in the heart using a display device. The graphical indicators of the plurality of Shannon entropy values can include a range of different colors, shades of a gray or another color, different symbols, or indexed values. Each of such visual elements of the range can correspond to a Shannon entropy value such that the displaying of the graphical indicators of the plurality of Shannon entropy values shows Shannon entropy levels at different locations in the heart.

Figure 5:
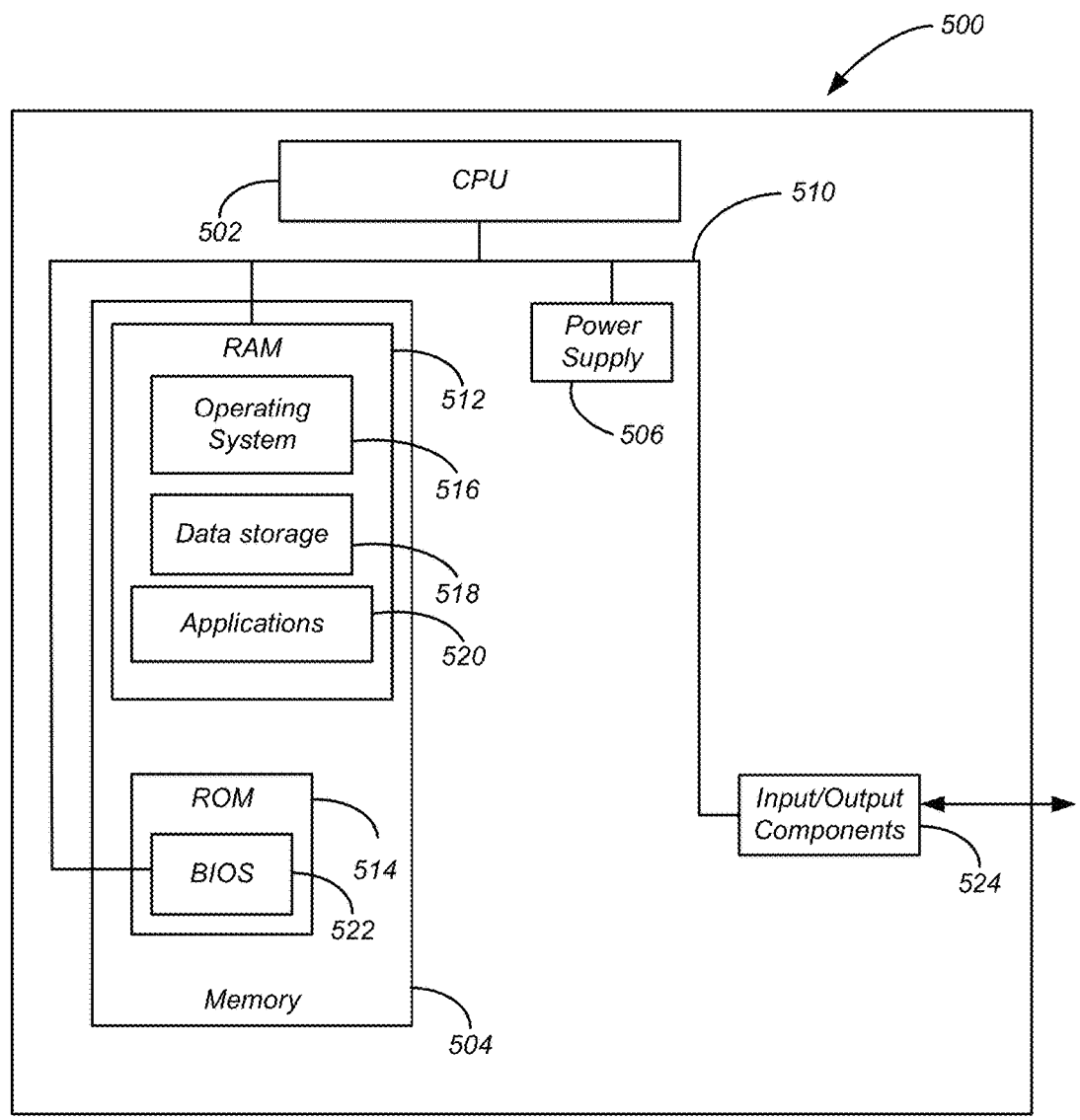
FIG. 5 illustrates a block diagram of an example device that can implement at least some of the operations illustrated in FIG. 1.

At 108, the entropy map is displayed on a display device, such as the monitor or display device (see for example input/output components 524 of FIG. 5 which may include a display device). According to the entropy dataset and/or map, the processor automatically (or a user manually) can identify a pivot point or some other aspect of a rotor in a fibrillation at 110 (such as shown by FIGS. 2A and 2B). In an example where the processor automatically identifies a pivot point or some other aspect of the rotor, the actual map may not be displayed. In other words, in automated identification of a rotor part displaying of the map is not necessary.

Finally, at 112, the system can physically change the heart at one or more of the locations of the aspects of the rotors (such as at the locations of pivot points) according to the analysis such as according to the entropy dataset or map. In exemplary embodiments, the changing of the heart can include catheter ablations at the locations of the pivot points of the rotors in the heart.

In an exemplary embodiment, the methods disclosed herein can use a symbolic dynamics approach that is based on if fluctuations of two or more time series are governed by different underlying dynamics then the derivations of corresponding symbolic sequences are not related. Histograms of resulting symbolic sequences can give a reconstruction of the sequences respective histories and provide a visual representation of intrinsic dynamic patterns. These intrinsic dynamics can be ignored in the time domain and frequency domain analysis, which can be the basis for existing signal processing techniques for rotor identification.

The process of symbolization can be used to represent any possible variation over time, depending on the number of symbols (such as amplitude bins) and the sequence lengths used. Thus, such symbolic dynamics can be independent of any assumptions about the nature of the signals. Symbolic dynamics approach can be applied to time series data obtained from the experiments disclosed herein to generate the histograms, as shown in FIG. 1 at 104.

Symbols can be created by amplitude bins and the information content of these symbols can be captured by SE. SE is also a statistical measure of information content that can be based on the distribution of amplitude values within the signal histogram for example.

The spatial uncertainty of wave front direction in a part of a rotor, such as the pivot zone or point of a rotor, can lead to information uncertainty in a bipolar electrogram from that part. For instance, the changing wave front direction near the pivot zone or point may cause a broader distribution in the bipolar voltage histogram. This may cause a pivot point or zone to have a higher SE value when compared to signals from the periphery of the rotor.

SE measures the distribution of signal values from electrograms within the histogram. Each electrogram from different spatial location can be binned, such as by using a bin size of 0.001 mV, according to its amplitude into a voltage histogram (as shown in FIG. 1 at 104 and 104a). Then, the relative probability density 'p' may be defined (as shown in FIG. 1 at 104c), such as according to the number of counts in an amplitude bin divided by the sum of bin counts in all the bins. SE values can be calculated for the intra-atrial electrograms or other types of datasets using Equation (1) disclosed herein.

The SE values estimated using Equation (1) can then be used to generate a 2D or 3D SE map depending on the implementation, such as shown in FIG. 1 at 106b. The SE map can then be displayed via a display device at 108. As illustrated by FIG. 1, the SE map can continuously update itself as new time series data is inputted into the system or as the analysis of symbols at 106 reoccurs. Note that 106a and 106b may be sub-operations of 106. Also, note that 104a, 104b, and 104c may be sub-operations of 104.

In an example, the aforementioned maps can be generated by using the calculated SE values, such as from MATLAB, and re-annotating them exactly to the carto points (such as by using the GE Prucka system from which the raw intra-atrial electrograms were obtained). This can be accomplished manually or automatically. Subsequent to such annotation, the annotated SE data can then be superimposed on the anatomical map to obtain a full 3D SE distribution in the atria by interpolation between the CARTO points for visualization and color coded to represent the range of SE values. The estimated SE values can be multiplied by a factor of 10 for display purposes. The CARTO software also allows 3D viewing of a 3D entropy map for visualization and interpretation to identify potential active sites that may cause and maintain AF.

As mentioned herein, FIG. 2A illustrates an example of a single rotor in an isolated rabbit heart from optical mapping experiments. In FIG. 2A, the pivot point of the rotor is indicated by an arrow. FIG. 2B illustrates a corresponding 2D normalized SE map showing correct identification of the pivot point (the arrow) illustrated in FIG. 2A. FIG. 2A is an example snapshot of a phase movie, where different colors represent different phases of action potential. The convergence of different phases may correspond to a singularity point, e.g., the pivotal point or core of the rotor, which can be identified by the arrow. FIG. 2B shows an example 2D SE map calculated for the same rotor illustrated in FIG. 2A. In FIG. 2B, the SE values are normalized to a maximum value for better visualization. Note that an SE map can provide for direct identification of the core or the rotor (see the arrow). Also, note that the SE values are minimal at the core of the rotor, and a ring of high SE values may surround an area of low SE at the core of the rotor.

Figure 3:
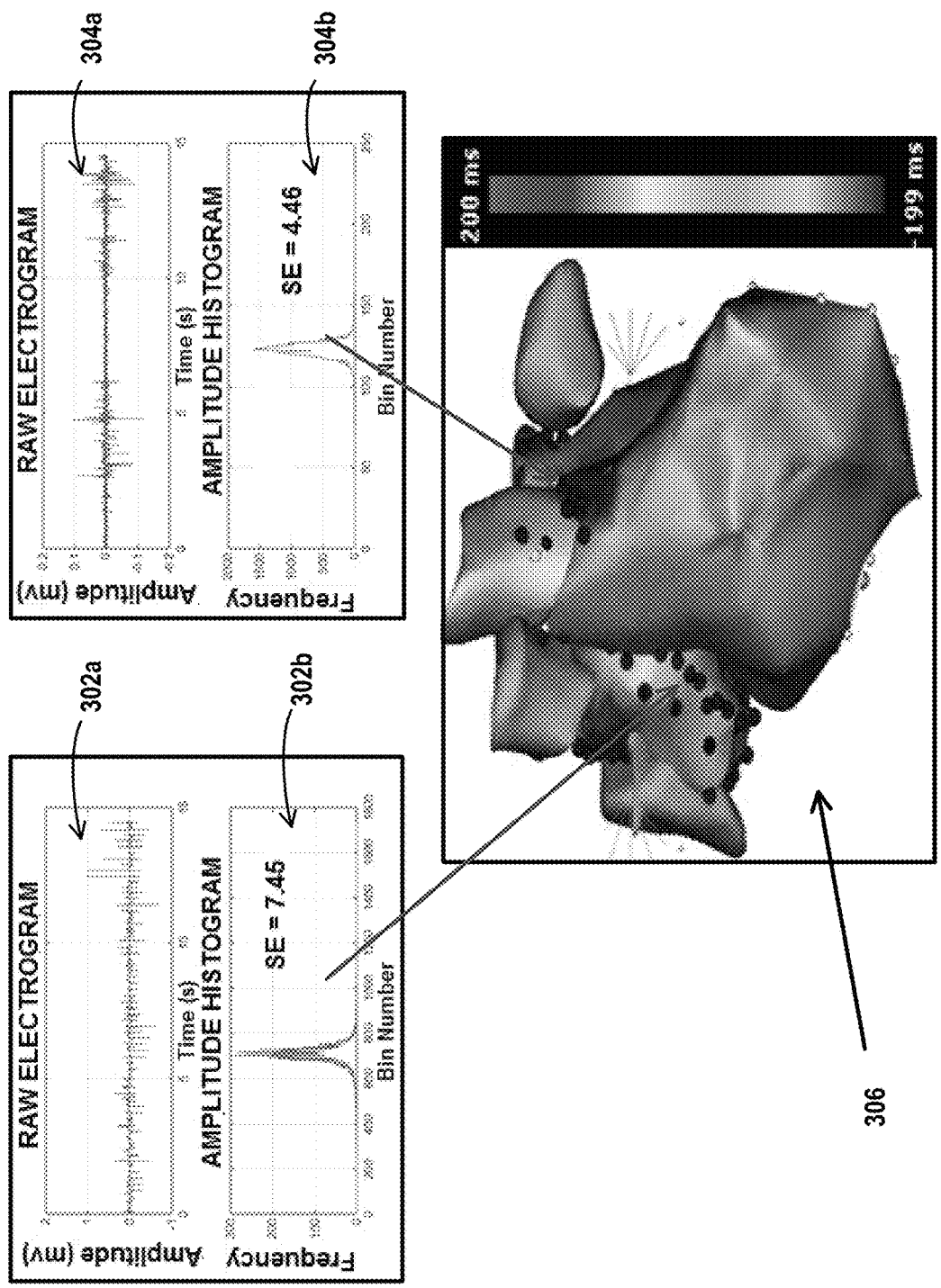
FIG. 3 illustrates examples of raw electrograms, amplitude histograms, and a 3D distribution of a LAT from a CARTO system.

FIG. 3 illustrates raw intra-atrial electrogram charts 302a and 304a from a carto point in LA, amplitude histograms 302b and 304b of the corresponding electrograms, and corresponding SE values. Also shown, is an image 306 of distribution of LAT in the right anterior oblique (RAO) views obtained from a CARTO system.

FIG. 4 illustrates a 3D SE distribution of the atria showing higher regions at the base of right atrial appendage. Note that for visualization purposes, SE was multiplied by 10. FIG. 4 also shows the 3D SE distribution in the atria superimposed on the anatomical map. Higher regions of SE are located at the base of right atrial appendage (see area with the bluish pink color). Other areas have lower SE values (see green and yellow color). FIG. 4 also provides that current catheter mapping system could be used for implementing a novel SE-based approach for rotor mapping to identify active rotor sites. It is seen that SE values were particularly higher outside the PV area which could indicate active sites, and the visualization of this 3D map could provide an opportunity for the clinical electro physiologist to investigate optimal approaches for ablation strategies.

In examples, the symbolic dynamic approach can be used to develop a more robust spatiotemporal mapping system using entropy to address the inherent limitations of other approaches for mapping. Entropy approach using the optical mapping data with known rotor pivot zones can demonstrate feasibility to accurately identify rotor core area. Results of applying such validated approaches to human persistent AF data may show that SE provides differentiable areas which have lower and higher entropy values. These results can be superimposed directly on a 3D anatomical map provided direct visualization of an anatomically accurate 3D entropy map.

Higher region of entropy can be at the base of the right atrial appendage which could indicate the presence of active AF causing sites, which is outside the PV area. Although a causal relationship has not been established, it can be inferred that for persistent AF patients the active triggers that cause AF may arise from outside PV regions explaining why conventional ablation strategies targeting PV area have failed in the past.

FIG. 5 illustrates a block diagram of an exemplary electronic device 500 that can implement aspects of methods disclosed herein that can provide operations, such as one or more of the operations described herein including those illustrated in FIG. 1. The electronic device 500 can include a central processing unit (CPU) 502, memory 504, a power supply 506, and input/output components 524, and a communication bus 510 that connects the aforementioned elements of the electronic device. The CPU 502 can be any type of data processing device or processor, such as a CPU. Also, the CPU 502 can include one or more data processing devices or processors that may be in combination with local or remote memory. Also, for example, the CPU 502 can be central processing logic. The memory 504, which can include random access memory (RAM) 512 or read-only memory (ROM) 514, can be enabled by one or more memory devices. The one or more memory devices may also be local or remote with respect to the electronic device 500 or the CPU 502. The RAM 512 can store data and instructions defining an operating system 516, data storage 518, and applications 520, such as applications implemented through hardware including circuitry that can implement the operations illustrated in FIG. 1. The applications 520 may include hardware (such as circuitry and/or microprocessors), firmware, software, or any combination thereof. The ROM 514 can include basic input/output system (BIOS) 522 of the electronic device 500. The memory 504 may, include a non-transitory medium executable by the CPU. For example, the memory 504 can include a non-transitory medium with instructions executable by a processor to cause the processor (such as the CPU) to perform any of the operations disclosed herein, such as the operations described with respect to FIG. 1.

The power supply 506 contains power components, and facilitates supply and management of power to the electronic device 500. The input/output components 524 can include circuitry for facilitating communication between any components of the electronic device 500, components of external devices, and end users. The I/O components 524 can include user interfaces such as monitors, keyboards, touchscreens, microphones, and speakers. Further, some of the I/O components 524 can facilitate communication between components of the electronic device 500, and can ease processing performed by the CPU 502. The bus 510 may provide such functionality as well.

The electronic device 500 can send and receive signals, such as via a wired or wireless network, or may be capable of processing or storing signals, such as in memory as physical memory states. The device 500 can include or be communicatively coupled to a server, dedicated rack-mounted servers, a personal computer, and/or an integrated device combining various features disclosed herein such as laboratory hardware or a medical device including an integrated computing device.

Experiments in accordance with embodiments of the method have been performed, such as those discussed in "Feasibility of visualizing higher regions of Shannon Entropy in Atrial Fibrillation patients", Conf Proc IEEE Eng Med Biol Soc. 2015 August; 2015:4499-502. doi: 10.1109/EMBC.2015.7319394. Such experiments have shown evidence of the successes using some of the disclosed techniques. Techniques based on entropy can correctly identify self-sustaining regions of chaotic rhythms in animal models of arrhythmia. Also, experimental verification of the feasibility of using a SE based mapping technique based on a symbolic dynamics approach to identify self-sustaining points of rotors in isolated animal hearts has been successful. Further, a mapping approach, such as one of the approaches disclosed herein, that was applied to clinical intra-cardiac electrograms from a patient with persistent AF to construct a 3-dimensional (3D) SE map has been successful. SE may correctly predict a specific part of a rotor, such as a pivot point, in an animal model.

Although the present disclosure has been described with reference to preferred embodiments, workers skilled in the art will recognize that changes may be made in form and detail without departing from the spirit and scope of the present disclosure.

What is claimed is:

1. A method for graphically indicating pivot points of rotors associated with atrial or ventricular fibrillation, comprising:
   receiving, using a processor, an electrogram for each of a plurality of spatial locations in a heart, each electrogram comprising time series data including a plurality of electrical potential readings over time;
   generating, from the time series data, an entropy dataset including a plurality of Shannon entropy values corresponding to the plurality of spatial locations in the heart; and
   generating, from the entropy dataset, an entropy map including a plurality of graphical indications of the Shannon entropy values at the plurality of spatial locations in the heart, wherein the entropy map includes an image of the heart and graphical indications of locations of the pivot points of the rotors in the heart.

2. The method of claim 1, further comprising physically changing the heart at one or more of the plurality of spatial locations in the heart according to the entropy dataset.

3. The method of claim 2, wherein the changing of the heart includes catheter ablations at the one or more of the plurality of spatial locations in the heart.

4. The method of claim 1, further comprising performing the plurality of electrograms at the plurality of spatial locations in the heart to obtain the time series data.

5. The method of claim 1, further comprising displaying graphical indicators of the plurality of Shannon entropy values corresponding to the plurality of spatial locations in the heart using a display device.

6. The method of claim 5, wherein the graphical indicators of the plurality of Shannon entropy values include a range of different colors, shades of a gray or another color, different symbols, or indexed values each of the range corresponding to a Shannon entropy value such that the displaying of the graphical indicators of the plurality of Shannon entropy values shows Shannon entropy levels at different locations in the heart.

7. The method of claim 1, wherein the plurality of electrograms is derived from an optical mapping experiment on the heart.

8. The method of claim of claim 1, wherein the generating of the entropy dataset includes:
   binning the plurality of electrograms according to amplitude, which results in a plurality of bins per binned electrogram, wherein a bin of the plurality of bins represents an amplitude or amplitude range and includes a frequency of occurrences of the amplitude or amplitude range;
   determining a probability density of each bin of the plurality of bins, per binned electrogram; and
   determining a Shannon entropy value according to the determined probability densities, per binned electrogram,
      wherein the determining of the Shannon entropy value includes using the following equation:

$$SE = -\sum_{i=0}^{N-1} p_i \log_2 p_i,$$

and wherein N is a number of bins in the plurality of bins per binned electrogram, and $p_i$ is a probability of a sample reading falling within a particular bin of the plurality of bins.

9. A method for graphically indicating aspects of rotors associated with atrial or ventricular fibrillation, comprising:
   receiving, using a processor, an electrogram for each of a plurality of spatial locations in a heart, each electrogram comprising time series data including a plurality of electrical potential readings over time;
   binning the plurality of electrograms according to amplitude, which results in a plurality of bins per binned electrogram, wherein a bin of the plurality of bins represents an amplitude or amplitude range and includes a frequency of occurrences of the amplitude or amplitude range;
   determining a probability density of each bin of the plurality of bins, per binned electrogram;
   determining a Shannon entropy value according to the determined probability densities, per binned electrogram;
   generating an entropy dataset including the Shannon entropy values corresponding to the plurality of spatial locations in the heart; and
   generating, from the entropy dataset, an entropy map including a plurality of graphical indications of the Shannon entropy values at the plurality of spatial locations in the heart, wherein the entropy map includes an image of the heart and graphical indications of locations of the pivot points of the rotors in the heart.

10. The method of claim 9, further comprising physically changing the heart at one or more of the plurality of spatial locations in the heart according to the entropy dataset.

11. The method of claim 10, wherein the changing of the heart includes catheter ablations at the one or more of the plurality of spatial locations in the heart.

12. The method of claim 9, further comprising performing the plurality of electrograms at the plurality of spatial locations in the heart to obtain the time series data.

13. The method of claim 9, further comprising displaying graphical indicators of the plurality of Shannon entropy values corresponding to the plurality of spatial locations in the heart using a display device, wherein the graphical indicators of the plurality of Shannon entropy values include a range of different colors, shades of a gray or another color, different symbols, or indexed values, each of the range corresponding to a Shannon entropy value such that the displaying of the graphical indicators of the plurality of Shannon entropy values shows Shannon entropy levels at different locations in the heart.

14. The method of claim 9, wherein the determining of the Shannon entropy value uses the following equation:

$$SE = -\sum_{i=0}^{N-1} p_i \log_2 p_i,$$

wherein N is a number of bins in the plurality of bins per binned electrogram, and $p_i$ is a probability of a sample reading falling within a particular bin of the plurality of bins.

15. The method of claim 9, further comprising:
   generating a histogram of the plurality of bins;
   communicating the histogram to a display device communicatively coupled to the processor; and
   graphically displaying the histogram by the display device.

16. A non-transitory computer readable medium for graphically indicating aspects of rotors associated with atrial or ventricular fibrillation, comprising:
   instructions executable by a processor to receive an electrogram for each of a plurality of spatial locations in a heart, each electrogram comprising time series data including a plurality of electrical potential readings over time;
   instructions executable by a processor to generate, from the time series data, an entropy dataset including a plurality of Shannon entropy values corresponding to the plurality of spatial locations in the heart; and
   instructions executable by a processor to generate, from the entropy dataset, an entropy map including a plurality of graphical indications of the Shannon entropy values at the plurality of spatial locations in the heart, wherein the entropy map includes an image of the heart and graphical indications of locations of the pivot points of the rotors in the heart.

17. The non-transitory computer readable medium of claim 16, wherein the instructions to generate the entropy dataset include:
   instructions executable by a processor to bin the plurality of electrograms according to amplitude, which results in a plurality of bins per binned electrogram, wherein a bin of the plurality of bins represents an amplitude or amplitude range and includes a frequency of occurrences of the amplitude or amplitude range;
   instructions executable by a processor to determine a probability density of each bin of the plurality of bins, per binned electrogram; and
   instructions executable by a processor to determine a Shannon entropy value according to the determined probability densities, per binned electrogram, and according to the following equation:

$$SE = -\sum_{i=0}^{N-1} p_i \log_2 p_i,$$

wherein N is a number of bins in the plurality of bins per binned electrogram, and $p_i$ is a probability of a sample reading falling within a particular bin of the plurality of bins.

\* \* \* \* \*

UNITED STATES PATENT AND TRADEMARK OFFICE
CERTIFICATE OF CORRECTION

PATENT NO. : 10,258,249 B2
APPLICATION NO. : 15/373193
DATED : April 16, 2019
INVENTOR(S) : Alena Talkachova et al.

Page 1 of 1

It is certified that error appears in the above-identified patent and that said Letters Patent is hereby corrected as shown below:

In the Claims

Claim 8
Column 13, Line 7, after "method", delete duplicative "of claim".

Signed and Sealed this
Twelfth Day of May, 2020

Andrei Iancu
*Director of the United States Patent and Trademark Office*